US010809162B2

(12) United States Patent
Eicher et al.

(10) Patent No.: US 10,809,162 B2
(45) Date of Patent: Oct. 20, 2020

(54) TESTING SYSTEM AND TESTING METHOD

(71) Applicant: BOEHRINGER INGELHEIM MICROPARTS GMBH, Dortmund (DE)

(72) Inventors: Joachim Eicher, Ingelheim am Rhein (DE); Jutta Eigemann, Dortmund (DE); Johannes Geser, Gerlingen (DE); Andreas Peters, Bochum (DE); Hans-Juergen Koelbel, Siegburg (DE)

(73) Assignee: Boehringer Ingelheim Microparts GmbH, Ingelheim am Rhein (DE)

( * ) Notice: Subject to any disclaimer, the term of this patent is extended or adjusted under 35 U.S.C. 154(b) by 22 days.

(21) Appl. No.: 15/765,895

(22) PCT Filed: Oct. 6, 2016

(86) PCT No.: PCT/EP2016/073834
§ 371 (c)(1),
(2) Date: Apr. 4, 2018

(87) PCT Pub. No.: WO2017/060328
PCT Pub. Date: Apr. 13, 2017

(65) Prior Publication Data
US 2019/0113418 A1 Apr. 18, 2019

(30) Foreign Application Priority Data

Oct. 9, 2015 (EP) .................................... 15189068
May 12, 2016 (EP) .................................... 16169471

(51) Int. Cl.
*G01M 99/00* (2011.01)
*A61M 15/00* (2006.01)
(Continued)

(52) U.S. Cl.
CPC ...... *G01M 99/008* (2013.01); *A61M 15/0065* (2013.01); *B05B 11/0062* (2013.01);
(Continued)

(58) Field of Classification Search
CPC ............. G01M 99/008; B05B 11/3042; B05B 11/3052; B05B 11/3091
(Continued)

(56) References Cited

U.S. PATENT DOCUMENTS 2,863,316 A * 12/1958 Abplanalp .............. G01M 3/34 73/45
5,833,088 A 11/1998 Kladders
(Continued)

FOREIGN PATENT DOCUMENTS

DE 10136554 A1 2/2003
EP 2381237 * 10/2011 ............. G01N 15/02
(Continued)

OTHER PUBLICATIONS

Abstract in English for EP 2381237, dated Oct. 26, 2011.
International Search Report and Written Opinion for corresponding application PCT/EP2016/073834, dated Dec. 1, 2016.

*Primary Examiner* — Benjamin R Schmitt
(74) *Attorney, Agent, or Firm* — Matthew B. Dernier, Esq.

(57) ABSTRACT

A system for testing the proper functioning of an atomiser for dispensing a fluid in the form of an aerosol is proposed, wherein the system comprises the atomiser and a test apparatus, wherein the atomiser comprises a container holding the fluid, and a housing part for inserting and/or replacing the container, wherein the container is movable relative to the housing part in order to dispense the fluid and the test apparatus comprises a measuring device for measuring the movement of the container when the fluid is dispensed. In addition, a method for testing the proper functioning of an
(Continued)

atomiser for dispensing a fluid in the form of an aerosol is proposed, wherein the atomiser comprises a container holding the fluid, and a housing part for inserting and/or replacing the container, wherein the container is moved relative to the housing part in order to dispense the fluid and the movement of the container is measured and/or analysed when the fluid is dispensed.

18 Claims, 4 Drawing Sheets

(51) Int. Cl.
    *B05B 11/00*         (2006.01)
    *B05B 15/40*         (2018.01)

(52) U.S. Cl.
    CPC .......... *B05B 11/3091* (2013.01); *B05B 15/40* (2018.02); *A61M 2209/02* (2013.01); *B05B 11/0038* (2018.08); *B05B 11/00412* (2018.08); *B05B 11/3015* (2013.01)

(58) Field of Classification Search
    USPC .................................................. 73/52, 865.9
    See application file for complete search history.

(56) References Cited

U.S. PATENT DOCUMENTS

| | | |
|---|---|---|
| 2003/0034032 A1 | 2/2003 | Ziegler |
| 2004/0231667 A1 | 11/2004 | Horton et al. |

FOREIGN PATENT DOCUMENTS

| | | |
|---|---|---|
| EP | 2381237 A1 | 10/2011 |
| WO | 9606011 A2 | 2/1996 |
| WO | 2004091806 A1 | 10/2004 |
| WO | 09047173 A2 | 4/2009 |

* cited by examiner

TESTING SYSTEM AND TESTING METHOD

The present invention relates to a system or test system for testing the proper functioning of an atomiser for dispensing a fluid in the form of an aerosol according to the preamble of claim 1, to a method or test method for testing the proper functioning of an atomiser for dispensing a fluid in the form of an aerosol according to the preamble of claim 10, and to a test apparatus according to claim 16.

The term "atomiser" should preferably be taken to mean a structural device designed in particular to atomise a fluid, in particular a medicinal product formulation, or change said fluid into an aerosol. Particularly preferably, an atomiser within the meaning of the present invention is an inhaler for inhaling a fluid in the form of an aerosol. Preferably, an atomiser within the meaning of the present invention comprises a container as a reservoir for a fluid to be atomised. The container can preferably be inserted into the atomiser (e.g. by opening a cover or the like), is arranged therein in an accessible manner, or is replaceable. At this juncture, the atomiser is in particular considered to be an atomiser in which the container is movable, preferably axially, relative to the housing or housing part in order to dispense the fluid. WO 09/047173 A2 discloses an example of such an atomiser.

When a fluid, in particular a liquid medicinal product formulation, is atomised by means of an atomiser of the type mentioned at the outset, as precise an amount of active ingredient as possible should be changed into an aerosol to be inhaled. The aerosol produced in this manner should be distinguished by having a low average droplet size with a narrow droplet size distribution, and a low impulse or low dispersal rate. Preferably, the droplets produced in this manner have a droplet diameter of less than 5 μm, in particular between 2 μm and 5 μm, since droplets of this size are suitably deposited in pulmonary systems when inhaled.

Within the meaning of the present invention, the term "fluid" should be understood and construed in a broad manner. In particular, the term "fluid" covers liquid solutions, as well as dispersions, suspensions or the like.

In the present invention, the term "aerosol" should preferably be taken to mean a cloud-like or mist-like accumulation of a multiplicity of droplets of a fluid that has preferably been atomised by means of an atomiser, the droplets preferably having a low velocity and/or at least substantially random movement directions. An "aerosol" can, for example, have or form a conical droplet cloud, the main dispersal direction of the droplet cloud in particular at least substantially matching the main discharge direction or discharge pulse direction.

When manufacturing or producing atomisers of the type mentioned at the outset, it is necessary, for example as part of quality control, to check the atomisers for faults or to check that they are functioning properly and/or to discard faulty or fault-prone atomisers, for example in a full or 100% inspection and/or as part of sample inspections.

The term "proper functioning" should preferably be taken to mean the capabilities of the atomiser that are necessary for the fluid to be dispensed or atomised by means of the atomiser, or for the intended purpose or function to be fulfilled. Preferably, the proper functioning of the atomiser corresponds to the degree to which requirements on the atomiser or on the (target) function(s) of the atomiser can be met.

Preferably, the proper functioning is checked using measurements detected during an actuation of the atomiser. Particularly preferably, target values and/or limits within which the measured values of a functional atomiser may fall are set, for example as part of quality control.

Primarily, a functional atomiser for producing an inhalable aerosol should dispense a specified amount of fluid or medicinal product formulation in the form of an aerosol cloud or spray mist that has specified properties. This basic functionality of the atomiser can be checked using measurements taken on the aerosol cloud or spray mist produced, for example by means of direct measurements of droplet size distributions (e.g. by means of optical methods or cascade impactors), measurements of the total weight of fluid dispensed in the spray mist, etc.

In some atomisers, e.g. in nose spray pumps, the properties of the spray mist, such as spray pattern, geometry of the spray cloud or droplet size distribution, may depend on how the atomiser or pump is triggered. In conventional nose spray pumps, an upper part containing the outlet opening is pushed towards a drug container counter to a restoring force in order to trigger the pump. In this case, slow actuation would likely lead to the fluid flowing out with only slight cloud formation, and very fast actuation could produce a spray mist that is so thin that many of the droplets are inhaled into deeper airways instead of being adsorbed at the nasal mucosa. For the proper functioning of such a nose spray pump to be checked according to certain criteria without this separate intervention from the user, as required as part of clinical approval, WO2004/091806 A1 proposes the use of an apparatus in which a nose spray pump of this kind or "metered dose inhaler" (MDI) can be triggered in a mechanically controlled manner. By means of the adjustability of this actuation, the apparatus makes it possible, in combination with measurements taken at the atomiser, to examine the relationship between the mechanical interaction of the movable and immovable atomiser parts and the functioning of the atomiser. For this purpose, the analysis of spray patterns on thin-layer chromatography plates (TLC) is described as the measurement method, for example. In this way, it is possible to generate data that can be used to define parameters for automatic trigger systems that reduce fluctuations in routine inspections (by comparison with trigger processes carried out manually by the tester).

DE 10136554 A1 discloses a laboratory method for determining the particle size distribution in an aerosol from an inhaler, and an apparatus for carrying out the method. This document proposes measuring the particle size of aerosol particles by means of laser diffraction analysis or a laser diffraction method. In this case, measurement conditions are established that recreate the realistic conditions when a patient uses the inhaler as intended, i.e. in particular the high air moisture levels in the human oropharyngeal area. EP 2381237 A1 discloses a laboratory measurement method that builds on the above method and in which the determination of the respirable portion of the aerosol (fine particle portion) is combined with a measurement of the duration of spray. During the particle measurement in this case, scattered laser light is focused towards a semiconductor detector by a converging lens and is analysed by means of analysis methods based on the Mie scattering theory or the Fraunhofer method.

Other possible examples of measurement variables are the flow rate in the atomiser nozzle ducts, the dispensed volume and/or dispensed weight of fluid, in particular per triggering and/or per unit of time, the volume and/or weight of fluid in the atomiser that leaks out and/or the fluid pressure and/or fluid pressure drops within the atomiser. In some cases, measuring such measurement variables directly is complex and thus only possible to a limited extent in batch production processes, such as in particular an automated inspection and/or a 100% inspection or 100% screening inspection.

Against this background, the object of the present invention is to provide a test system and a test method for testing the proper functioning of an atomiser, any atomiser faults preferably being able to be identified, defined, assessed and/or indexed or being identified, defined, assessed and/or indexed in a simple, cost-effective, quick and/or reliable manner.

In particular, the test method and test system should be suitable for use in a batch production process.

The aforementioned object is achieved by a test system according to claim 1, a test method according to claim 10 or a test apparatus according to claim 16. The dependent claims relate to advantageous developments.

The test apparatus according to the invention or the system according to the invention for testing the proper functioning of an atomiser preferably comprises an atomiser and a test apparatus for testing the atomiser.

In one aspect of the present invention, as part of a functionality inspection, the proper functioning of the atomiser is tested at least in part using measurements taken on the atomiser itself, preferably on one or more movable parts of the atomiser (in particular on parts that are moved during the actuation). In this regard, measured values are preferably detected for measurement variables for which there is a correlation with properties of the spray mist in particular owing to the operating principle of the corresponding atomiser. As a result, it is possible to provide an apparatus for testing the proper functioning of the atomiser or a test system in which the measurement times are at most slightly longer than the times required for actuating the atomiser. Preferably, this functionality inspection takes place in an in particular automated 100% inspection or 100% screening inspection.

According to the invention, for an atomiser in which a container holding the fluid to be dispensed moves while the fluid is being dispensed, the movement of the container is measured and the measured values detected by means of the associated measuring device are compared with target values and/or limits in a data processing device (e.g. in a computerised manner). If the measured values do not comply with the target values (specified in particular together with deviation ranges) and/or the measured values are outside a range defined by the limits, the atomiser is identified as being faulty in or by the test system and preferably automatically discarded. If the electronics of an automated system of this kind are designed appropriately, the cycle time of an atomiser is substantially determined by the duration of the actual measurement, which is terminated according to the invention when all the fluid/spray has been dispensed. Therefore, the test method is well suited to use in batch production, and also particularly suitable for use in a 100% inspection.

According to another aspect of the present invention, within the test system, measurements of this kind on the atomiser itself are combined with measurements on the aerosol cloud produced thereby or the spray mist produced thereby.

For this purpose, the test system preferably comprises a spray parameter measuring device and/or an imaging recording device that is connected to the data processing device of the system. In the spray parameter measuring device, predefined spray parameters are measured on the basis of spray photographs, the measured values being compared with predefined limits by means of the data processing device.

Alternatively or in addition, images from an imaging recording device are compared with reference images in the data processing device.

An atomiser is preferably automatically identified as being faulty (and in particular discarded) when the measured values or images detected for it do not comply with the target values or reference images and/or are outside a range defined by the limits or reference images.

Particularly preferably, light sections or light curtains are produced in the spray parameter measuring device for producing the spray photographs.

Preferably, in addition to the steps for assembling the atomiser, the production of the atomiser also includes a preferably automated screening inspection process, in which selected measurement variables that reflect the general functionality of the atomiser are measured, as well as a sampling step, in which a selected sample of atomisers undergo a detailed laboratory inspection. In a laboratory inspection of this kind, the selected atomisers are preferably tested to the point of destruction, while replicating a user usage pattern. In the process, the laboratory inspection also involves more complex measurements (by comparison with the screening inspection), such as in particular measurements of droplet size distribution, as known for example from DE 101 36 554 A1, and/or measurements of the weight of fluid discharged.

The atomiser preferably has the option of inserting and/or replacing a container holding a fluid (this option can, for example, be provided by an access opening in the housing of the atomiser and/or by a removable or openable housing part). Preferably, a user uses the atomiser together with a container that is in particular insertable and particularly preferably replaceable and holds a fluid, the container being movable relative to the housing part in order to dispense or atomise the fluid or to form an aerosol.

In the laboratory inspections, in which a user usage pattern is replicated, containers filled with a fluid that users wish to atomise are preferably used: For inhaler inspections, the containers are thus preferably cartridges filled with a liquid medicinal product formulation or a suitable placebo.

In 100% inspections or 100% screening inspections, however, the atomiser is preferably tested using inserted containers that contain a liquid or test liquid that can be removed from the atomiser in particular without leaving any residue (to prevent contamination or accumulation). The corresponding liquid, for example water or particularly preferably ethanol, should have a very high degree of purity. In the 100% inspections or 100% screening inspections, the atomiser preferably comprises a container that can interact with the test apparatus used. For this purpose, e.g. in the case of optical measurements, the container in particular comprises a suitable reflective surface (or a suitable conductivity or suitable magnetic properties in the case of electrical or inductive measurements, or suitable contours in the case of tactile or mechanical measurements, etc.). Optionally, the container comprises a readable label.

Preferably, the atomiser is based on an active atomisation principle; in particular, energy required for the atomisation is released from an energy storage mechanism and/or in particular the atomisation takes place automatically after a trigger button, a switch or the like on the atomiser is actuated.

To generate the pressure for the atomisation of the fluid, the atomiser particularly preferably comprises a mechanical pump mechanism, in particular a piston pump mechanism, the container preferably being moved together with a movable part of the pump mechanism. Preferably, the pump mechanism is combined with a spring acting as an energy storage mechanism.

In another aspect of the present invention, which can also be implemented independently, for the 100% inspection or 100% screening inspection, the system or test apparatus comprises a measuring device for preferably optically, mechanically and/or electrically and/or contactlessly measuring or detecting the movement of the container or of the container bottom of the atomiser when or while the fluid is atomised or dispensed, preferably in order to test the proper functioning of the atomiser.

Particularly preferably, the measuring device is designed to preferably optically, mechanically and/or electrically and/or contactlessly measure the velocity of the container or container bottom, the (axial) stroke of the container or container bottom, and/or the duration of the stroke. A test system that is particularly simple, quick and easily automated and/or can be integrated in a production process is thus provided.

In this case, the term "stroke" should be taken to mean the path or passage over a path between two end positions between which the container or container bottom moves, in particular between the situations before and after the atomiser is triggered.

The term "movement" should preferably be taken to mean the velocity of the container or container bottom, the stroke of the container or container bottom and/or the duration of the stroke of the container or container bottom when or while the fluid is dispensed or atomised. In particular, the movement of the container or container bottom covers the position of the container or container bottom as a function of the duration of the dispensing or atomisation of the fluid and/or the movement can be measured, defined and/or quantified by the position of the container or container bottom as a function of time. Most preferably, the test system or measuring device is designed to measure or quantify the movement, in particular the velocity, stroke and/or duration of the stroke of the container or container bottom when the fluid is dispensed, in particular by means of corresponding measured values.

Preferably, predefined target values for the container movement can be set for a functional or at least substantially fault-free atomiser. In this respect, measurement variables are preferably the container velocity, the container stroke (i.e. the movement path of the container) and/or the duration of the container movement corresponding to a container stroke. Preferably, these measurement variables or the interaction of these variables can be correlated with properties such as the flow rate in the atomiser nozzle ducts, the dispensed volume and/or dispensed weight of aerosol, in particular per triggering and/or per unit of time, the volume and/or weight of fluid in the atomiser that leaks out and/or the fluid pressure and/or fluid pressure drops within the atomiser.

For the measurement variables of a functional or at least substantially fault-fee atomiser, target ranges and/or limits are preferably specified, the target values, target ranges or limits preferably having been determined conceptually, empirically, numerically, practically and/or theoretically.

The present invention particularly preferably relates to testing an atomiser using a mechanical or manually actuable pump or a mechanical or manually actuable tensioning mechanism in order to pressurise the fluid or form the aerosol. In this case, a movement of the container can correspond to a piston movement of a pump, pressure generator or valve in the atomiser and/or a movement velocity of the container can correspond to a fluid dispensing rate. In principle, however, other mechanisms are also possible, in particular mechanisms in which the dispensed volume, dispensing rate and/or the properties of the aerosol correspond to characteristics of the container movement. It has proven particularly advantageous to check the proper functioning or compliance with target values or tolerance ranges by at least also using the container movement while the fluid is being dispensed.

The proposed method or test method for testing the proper functioning of the atomiser for dispensing a fluid in the form of an aerosol is also distinguished in that the movement of the container of the atomiser when the fluid is dispensed or atomised is measured, preferably by means of a measuring device, and/or analysed, preferably by means of a data processing device.

Particularly preferably, the velocity of the container or container bottom, the stroke of the container or container bottom and/or the duration of the container stroke when the fluid is dispensed or metered is measured and/or analysed and/or compared with target values, in particular a target velocity, a target stroke or target duration, and/or with limits, in particular a maximum and/or minimum velocity, a maximum and/or minimum stroke and/or a maximum or minimum duration. In this way, corresponding advantages are obtained.

Particularly preferably, the measuring device measures the movement of the container by means of optical triangulation. In this case, a visible modulated light spot is preferably projected onto the surface of the container bottom and an image of at least part of the reflection of this light spot is produced, in a position-sensitive manner, by a receiver optical system, which is arranged in particular at a specified angle, on a spatial resolution element (e.g. a CCD element) or sensor (contained in the receiver optical system). The distance of the container bottom is preferably calculated from the output signal of the sensor by means of a digital signal processor.

According to the invention, the measuring device and an associated data processing device are part of a preferably automated test apparatus in which the atomisers for which the detected measured values are outside the predefined limits are preferably automatically discarded as being faulty atomisers. The data processing device is thus designed to analyse measured values detected by the measuring device and/or to compare them with target values and/or limits and/or to identify the atomiser as being faulty within the test system when the measurements detected for it do not comply with the target values and/or are outside a range defined by the limits. For an atomiser identified as being faulty to be discarded, the system according to the invention comprises an ejection device into which the atomiser is preferably automatically slid and/or discarded after being identified as being faulty.

Another aspect of the present invention, which can also be implemented independently, relates to a test device for testing the proper functioning of an atomiser, the atomiser being designed to dispense a fluid in the form of an aerosol, the test device comprising a holding device for holding or gripping the atomiser, an actuation device for actuating the atomiser, a measuring device and a data processing device, the measuring device being designed to measure an atomiser part that moves when the fluid is dispensed, and the data processing device being designed to analyse measured values detected by the measuring device and/or to compare them with target values and/or limits and/or to automatically identify the atomiser as being faulty when the measured values detected do not comply with the target values and/or are outside a range defined by the limits.

According to another aspect of the present invention, which can also be implemented independently, a test apparatus is used to test the proper functioning of an atomiser, the atomiser being designed to dispense a fluid in the form of an aerosol and comprising a preferably insertable and particularly preferably replaceable container holding the fluid, and a housing part, the container being moved relative to the housing part in order to dispense the fluid and the movement of the container being measured when the fluid is dispensed. In this way, corresponding advantages are produced.

Further aspects, features, properties and advantages of the present invention will become apparent from the claims and the following description of a preferred embodiment given on the basis of the drawings, in which:

In the purely schematic drawings, which are not all to scale, the same reference numerals are used for like or similar components, matching or similar properties and advantages being obtained even if the description is not repeated.

Figure 1:
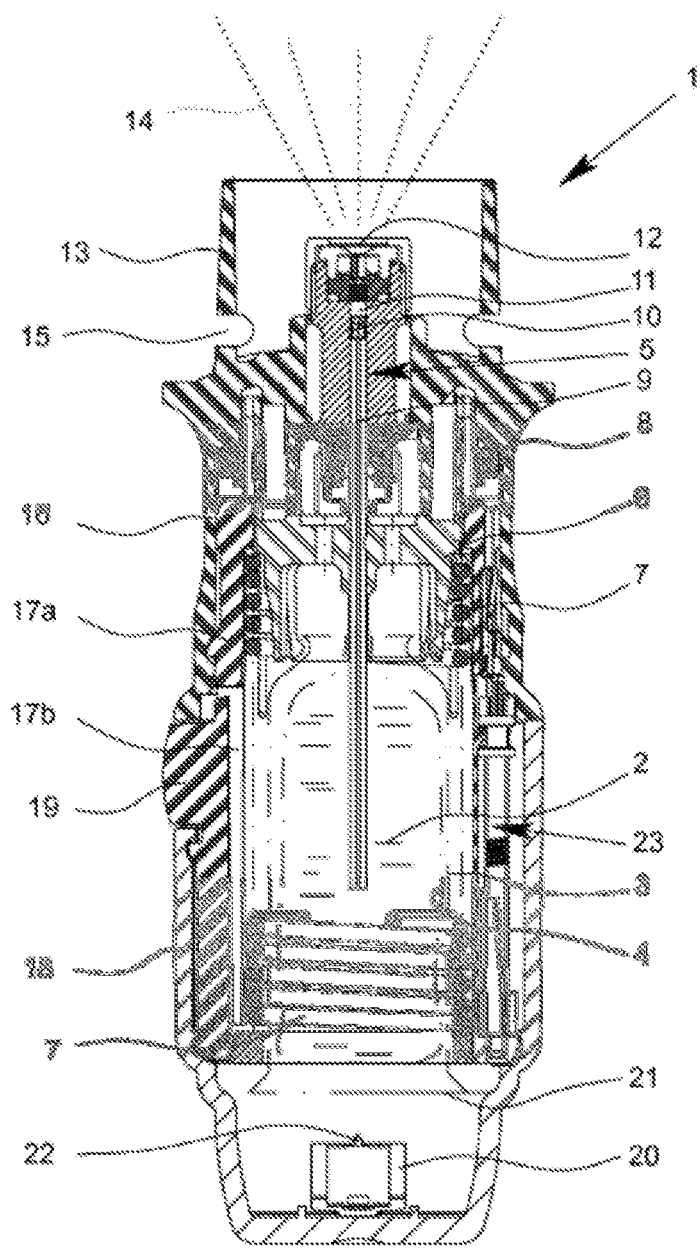
FIG. 1 is a schematic section through an atomiser in the non-tensioned state.
Figure 2:
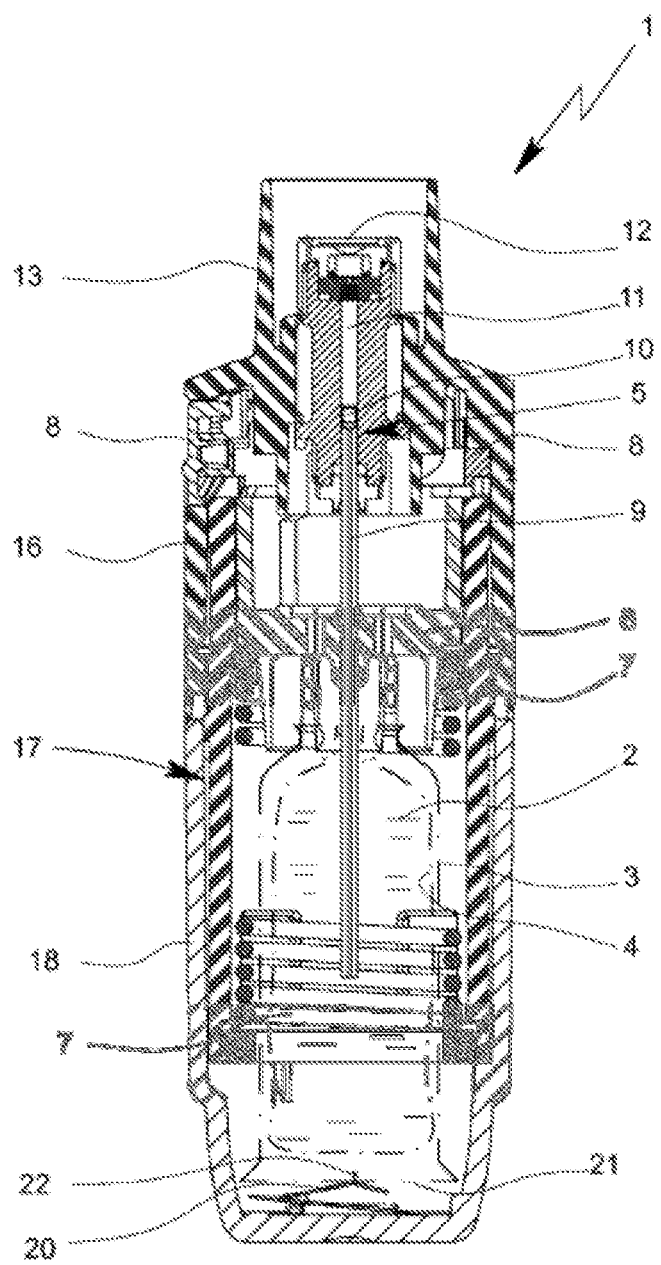
FIG. 2 is a schematic section through the atomiser in the tensioned state, rotated through 90° compared with FIG. 1.

FIG. 1 and FIG. 2 show an atomiser 1 for atomising a fluid 2, in particular a highly effective medicinal product or the like, the proper functioning of which can be tested for example in the test system or test method according to the invention. FIGS. 1 and 2 show the atomiser 1 in two states that occur when it is used by a user: FIG. 1 and FIG. 2 are schematic views of the atomiser 1 in the non-tensioned state (FIG. 1) and the tensioned state (FIG. 2). In this case, the terms "non-tensioned" and "tensioned" indicate the state of the energy storage mechanism contained in the atomiser 1 and preferably formed by a mainspring 7. In the "tensioned state" (FIG. 2), this energy storage mechanism is loaded to a certain extent and the atomiser 1 is ready to be triggered. The "non-tensioned" state (FIG. 1) shows the atomiser 1 in the triggered state (not ready for triggering).

In particular, the atomiser has a triggering option, in particular a trigger button 8a, upon the actuation of which the spray mist automatically or independently begins to be produced or the aerosol 14 automatically or independently begins to be dispensed.

Advantageously, the spray mist is thus not exposed to any influence, or only a negligible influence, from the handling of the atomiser 1 by the user/patient. In this embodiment, the atomiser 1 changes from the "tensioned" state to the "non-tensioned" state upon triggering or by the pressure from the trigger button 8a (while the fluid is being dispensed or the spray mist produced).

In particular, the atomiser 1 is formed as a portable inhaler and preferably operates without a propellant.

When the fluid 2, preferably a liquid, in particular a medicinal product, is atomised by means of the atomiser 1, an aerosol is preferably formed, a user or patient (not shown) in particular being able to inhale the atomised fluid 2 or aerosol 14, and fresh air preferably being able to be sucked into the mouthpiece 13 through at least one fresh air opening 15. Typically, the product is inhaled at least once a day, in particular several times a day, preferably at predefined intervals, particularly preferably depending on the patient's illness.

The atomiser 1 comprises a preferably insertable and preferably replaceable container 3 holding the fluid 2. The container 3 preferably forms a reservoir for the fluid 2 to be atomised.

Preferably, the container 3 (when used by the user or when in the states shown in FIGS. 1 and 2) contains a sufficient amount of fluid 2 or active ingredient to provide, for example, up to 200 metered units, i.e. up to 200 atomisations or uses, for example. A typical container 3, as disclosed in WO 96/06011 A2, holds a volume of from approximately 2 ml to 10 ml.

The container 3 is preferably at least substantially cylindrical or cartridge-shaped and can be inserted into the atomiser 1 from below after the atomiser has been opened, and can possibly be replaceable.

Preferably, the container 3 has a planar surface on its bottom, or the container 3 has a planar container bottom. Optionally, the container 3 has a metallic and/or reflective outer casing and/or a metallic and/or reflective container bottom or a metallic and/or reflective (outer) coating on the container bottom.

Preferably, the fluid 2 is held in the container 3 in a fluid chamber 4 formed by a collapsible pouch.

Preferably, the atomiser 1 also comprises a pressure generator 5 for conveying and atomising the fluid 2, in particular a predetermined, possibly adjustable metered amount in each case.

The pressure generator 5 preferably comprises a mount 6 for the container 3, an associated mainspring 7 (only shown in part) having a locking element 8 that can be manually actuated directly or preferably by means of a trigger button 8a for unlocking purposes, a supply tube 9 having a return valve 10, a pressure chamber 11 and a delivery nozzle 12 in the region of the mouthpiece 13. To trigger the atomiser, the locking element 8 is preferably slid transversely to the main axis of the atomiser 1/transversely to the movement direction of the moving parts of the pressure generator 5, or the trigger button 8a is pressed transversely to the main axis/movement axis. Advantageously, the forces to be applied for triggering thus do not contribute to the forces released upon triggering.

The container 3 is preferably secured, in particular latched, in the atomiser 1 by means of the mount 6 in such a way that the supply tube 9 enters the container 3. In this case, the mount 6 can be designed such that the container 3 can be detached and replaced.

When the mainspring 7 is axially tensioned, the mount 6 is moved downwards in the drawings together with the container 3 and the supply tube 9, and the fluid 2 is sucked out of the container 3 and into the pressure chamber 11 of the pressure generator 5 via the return valve 10.

When the spring is subsequently relaxed once the locking element 8 has been actuated, the fluid 2 in the pressure chamber 11 is pressurised since the supply tube 9 is moved back upwards again, together with its now closed return valve 10, as a result of the mainspring 7 relaxing, and now acts as a plunger. This pressure drives the fluid 2 out through the delivery nozzle 12, upon which it is atomised into an aerosol 14, as shown in FIG. 1.

Preferably, the supply tube 9 is held in position relative to the container 3 when in the use position, in particular by the mount 6. In particular, therefore, an (axial) movement of the supply tube 9 corresponds to an (axial) movement of the container 3.

When the supply tube 9 or the return valve 10 acts as a plunger, a movement of the supply tube 9 or container 3 corresponds to a volume displaced in the pressure chamber 11 or to a delivered or deliverable amount of fluid.

Taking particular account of the hydraulic properties of the atomiser 1 or the properties of the delivery nozzle 12 (e.g. nozzle geometry, hydraulic resistance formed by fitted filters and/or the delivery nozzle 12, etc.), conclusions can be drawn on the proper functioning of the atomiser 1 from the movement of the supply tube 9 or of the return valve 10 and/or another plunger and the corresponding movement of the container 3. In the atomiser 1 seen here in the embodiment, in order to produce the aerosol, the fluid 2 in the pressure chamber 11 and/or upstream of the delivery nozzle 12 is driven out through the delivery nozzle 12 under pressure and is thus expelled counter to the hydraulic resistance within this fluid pathway. In the process, the fluid pressure influences the resultant spray pattern or the properties of the aerosol 14. In this way, various functional faults, the detection of which in terms of the aerosol formation would in some cases otherwise require a plurality of different measurement methods, can be detected using the movement measurement for the piston of the pump of an atomiser 1 or, in this case, of the supply tube 9 or a container 3 that is attached thereto (and moved by the supply tube 9 together therewith). In this way, for example, the movement measurement can be used to discover leaks, the direct detection of which would otherwise require the weight of the discharged aerosol to be measured, for example, as well as incorrect positioning or blockages, which for example have an adverse effect on the duration of spray of the atomiser 1 and the quality of the spray mist (incorrect positioning increases the hydraulic resistance in the atomiser and the fluid is expelled more slowly from the pressure chamber). In the case of leaks, the fluid is not only expelled through the nozzle, but also through additional leak sites, thereby reducing the overall hydraulic pressure in the fluid paths within the atomiser (the fluid is thus expelled more quickly from the pressure chamber, i.e. a faster piston movement and shorter durations of spray are observed).

For an atomiser 1 having a piston pump mechanism, the duration of spray, i.e. the time for which the aerosol is produced at the delivery nozzle 12, is preferably determined by the time for which the piston (supply tube 9) or the container 3 connected thereto moves when the atomiser 1 is triggered or the spray mist produced. In this regard, the time that a container 3 moved together with the piston needs in order to move from its position in the tensioned instrument state to its position in the relaxed (non-tensioned) state when the atomiser 1 is triggered is preferably measured by means of an optical measurement method. The duration of this container movement substantially correlates with or corresponds to the duration of spray of the atomiser 1, since liquid is pressed outwards out of the atomiser 1 and through the delivery nozzle 12 during this movement.

The atomiser 1 preferably comprises a housing part 16 and an inner part 17 (FIG. 2) that is rotatable relative thereto and has an upper part 17*a* and a lower part 17*b* (FIG. 1), an in particular manually actuable lower housing part or a cover 18 in particular being detachably fastened to, in particular pushed on to, the inner part 17, preferably by means of a holding element 19.

To insert and/or replace the container 3, the lower housing part 18 is preferably detachable from the atomiser 1.

The lower housing part 18 can be rotated towards the housing part 16, the lower housing part preferably entraining the part 17*b*, which is lower in the drawing, of the inner part 17. As a result, the mainspring 7 is tensioned in the axial direction by means of a gearing (not shown) that acts on the mount 6. By means of the tensioning, the container 3 is preferably moved axially downwards until the container 3 assumes a final position indicated in FIG. 2. In this state, the mainspring 7 is tensioned.

Preferably, when the user or patient uses the atomiser and the tensioning is applied for the first time, a spring 20 acting axially and arranged in the lower housing part 18 abuts the container bottom 21 and, by means of a piercing element 22, pierces the container 3 or a seal on the bottom thereof when it comes into contact with the bottom for the first time, to allow air in. During the atomisation process, the container 3 is preferably moved back into its initial position by the mainspring 7.

The container 3 preferably performs a stroke movement during the tensioning process or for removing fluid and/or while the fluid 2 is being atomised or dispensed. Particularly preferably, while the fluid 2 is being atomised or dispensed, the container 3 moves by the stroke or stroke path $\Delta s_{stroke}$, at the preferably at least partly linear velocity $v_{stroke}$ and within the duration $\Delta t_{stroke}$, the duration $\Delta t_{stroke}$ preferably corresponding at least substantially to the time within which the fluid 2 is dispensed or atomised.

FIG. 3 is a schematic view of a proposed system 23 for testing the proper functioning of the atomiser 1.

The proposed system or test system 23 preferably comprises the atomiser 1 or at least components or modules of the atomiser 1, and a proposed test apparatus 24.

The atomiser 1 comprises a preferably insertable and preferably replaceable container 3 holding the fluid 2. The container 3 preferably forms a reservoir for the fluid 2 that is to be atomised during the test.

The container 3 is preferably at least substantially cylindrical or cartridge-shaped and can be inserted into the atomiser 1 and is replaceable or removable. In the example shown, a part of the container 3 is preferably directly accessible within the test system 23 for measurements.

The container 3 is preferably at least substantially rigid. Particularly preferably, the container 3 is made of a plastics material, in particular of a thermoplastic, most preferably of a polyether ether ketone. Preferably, the container 3 has a planar surface on its bottom, or the container 3 has a planar container bottom.

Optionally, the container 3 has a metallic and/or reflective outer casing and/or a metallic and/or reflective container bottom 21 or a metallic and/or reflective (outer) coating on the container bottom 21.

The test apparatus 24 is preferably designed to test the atomiser 1, in particular to check it is functioning properly and/or for any faults.

In particular, the system 23 or test apparatus 24 can be used to test or ascertain whether and/or to what extent the atomiser 1 is functional and/or meets predefined requirements or has predefined functions and/or whether the functioning of the atomiser 1 corresponds to the specifications defined for it or individually.

Particularly preferably, the system 23 or test apparatus 24 is designed to identify faulty atomisers 1 or those having impaired functions, preferably as part of the production or assembly of the atomiser 1. Most preferably, faulty atomisers 1 or those having impaired functions can be identified and/or (subsequently) discarded by the system 23 or test apparatus 24.

Preferably, the system 23 or test apparatus 24 is or can be integrated in the production or production process, in particular the assembly process, for the atomiser 1.

The system 23 or test apparatus 24 preferably comprises a holding device 25. The holding device 25 is preferably designed to hold, grip and/or receive the atomiser 1 or housing part 16 and/or the inner part 17, in particular in such a way as to make the atomiser 1 or at least the housing part 16 and/or the inner part 17 immovable relative to the holding device 25 when the fluid 2 is dispensed.

Preferably, the holding device 25 comprises a hole 26 in which at least part of the atomiser 1 is or can be received or is or can be inserted.

The system 23 or test apparatus 24 preferably comprises a measuring device 27, the measuring device 27 preferably being designed to measure the movement of the piston or the container 3 (supply tube 9) when the fluid 2 is dispensed.

The measuring device 27 is preferably designed as an optical, mechanical and/or electrical measuring device.

In particular, the measuring device 27 is designed to contactlessly, optically, mechanically and/or electrically measure the movement of the container 3 or container bottom 21, in particular the velocity $v_{stroke}$, the stroke $\Delta s_{stroke}$ and/or the duration $\Delta t_{stroke}$ of the stroke.

In particular, the measuring device 27 is designed to measure the movement of the container 3 or container bottom 21, in particular the velocity $v_{stroke}$, the stroke $\Delta s_{stroke}$ and/or the duration $\Delta t_{stroke}$ of the stroke, by means of triangulation. In particular, the measuring device 27 contains or is formed by a laser triangulation sensor system.

Preferably, the measuring device 27 comprises an emitter 28, in particular a laser or another source emitting radiation or electromagnetic waves, a sensor 29, and optionally an A/D converter, radiation detected by the sensor 29, images or other detected signals preferably being converted into one or more electrical signals by means of the A/D converter.

The sensor 29 can be designed in particular to detect a location or position and/or an angle and/or an intensity of the incident radiation or electromagnetic waves and to convert them into data or data signals such as measured values or measurement signals, in particular of the measuring device 27.

In particular, the sensor 29 is a CCD sensor, a CMOS sensor or the like.

The sensor 29 preferably comprises a plurality of distinguishable sensor portions, preferably arranged next to one another, known as pixels. The position or location of incident electromagnetic waves or incident light can thus be determined.

The sensor 29 preferably corresponds to the emitter 28 in such a way that the sensor 29 is capable of receiving, detecting and/or converting electromagnetic waves or radiation output by the emitter 28.

The sensor 29 can comprise an optical device, such as a lens, that preferably focuses electromagnetic waves in order to change the location and/or angle of incidence and/or intensity of incident electromagnetic waves or to more precisely define them (in particular to improve the analysis and/or precision at the sensor 29).

The emitter 28 and the sensor 29 are preferably arranged relative to one another and designed such that a movement of the container 3 or container bottom 21 leads to a change in the incident position, the angle of incidence and/or the incidence intensity of electromagnetic waves or radiation output by the emitter 28. This has proven particularly advantageous in precisely defining the location or position, movement and/or velocity of the container 3 or container bottom 21.

The emitter 28 is in particular designed to emit electromagnetic waves or radiation, in particular laser radiation, preferably towards the atomiser 1, in particular towards the container 3, particularly preferably towards the container bottom 21. Preferably, the emitter contains or is formed by a laser diode.

The measuring device 27 or emitter 28 is preferably arranged below the atomiser 1, in particular below the container 3 or container bottom 21, and/or oriented such that the atomiser 1, in particular the container 3 or container bottom 21, can be irradiated by means of the emitter 28.

In particular, the radiation emitted by the emitter 28 can be reflected by means of the container 3 or container bottom 21, preferably at least in part towards the sensor 29. Optionally, the container 3 or container bottom 21 has a reflective coating (not shown) for reflecting the radiation emitted by the emitter 28.

Figure 3:
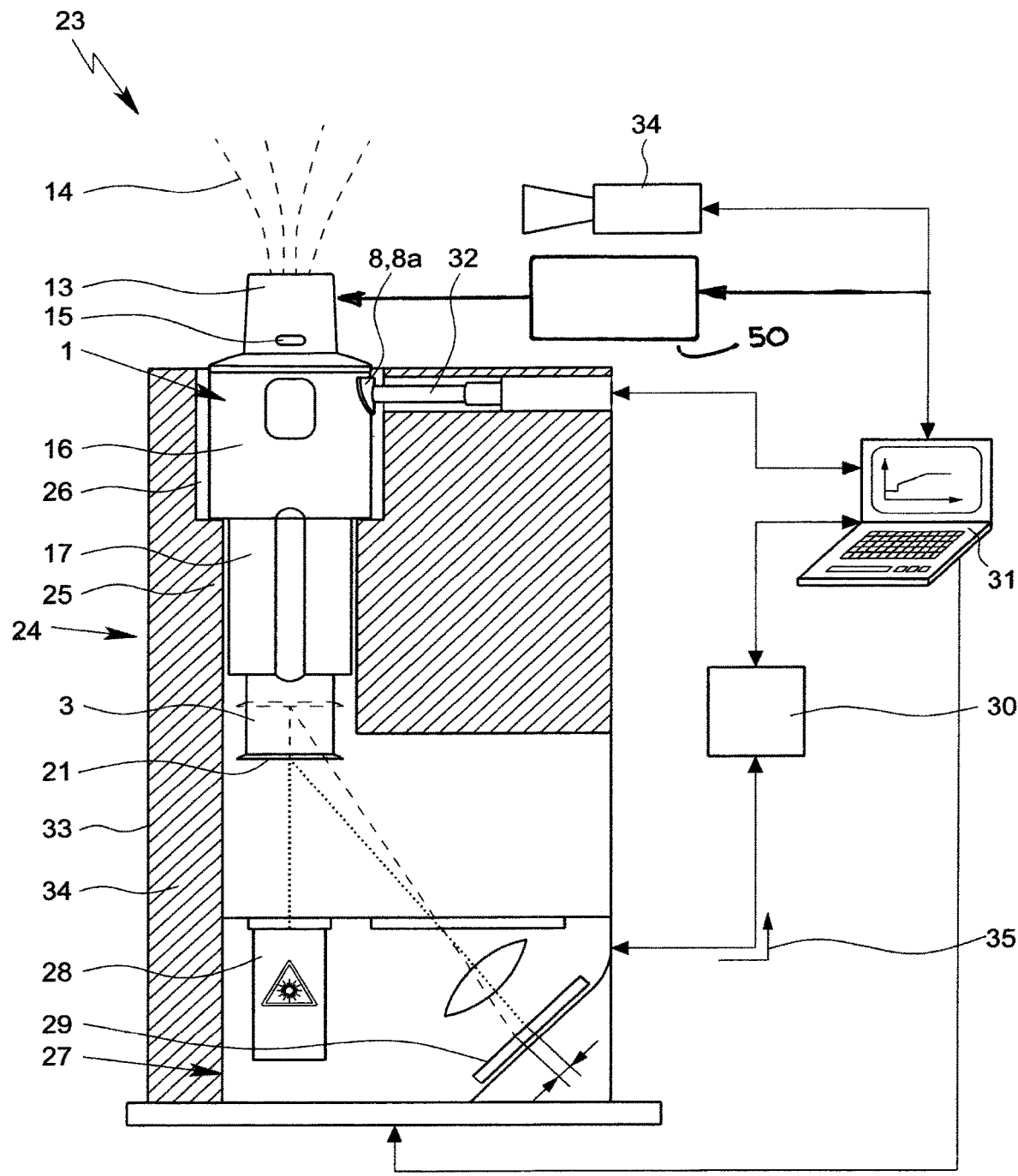
FIG. 3 is a schematic view of a proposed test system having the atomiser according to FIG. 1 and a proposed test apparatus.

Preferably, the emitter 28 is arranged relative to the atomiser 1 in such a way that the radiation emitted by the emitter 28 extends almost orthogonally to the container bottom 21 and/or almost in parallel with the movement axis of the container 3, as shown in FIG. 3.

In particular, the emitter 28 and the sensor 27 are arranged relative to the container bottom 21 in such a way that, in accordance with the principle that the angle of incidence equals the angle of reflection, the radiation emitted by the emitter 28 is reflected by the container bottom 21 towards the sensor 27, the emitter 28 and the sensor 27 preferably being arranged close together.

In the embodiment shown, the lower housing part 18 of the atomiser 1 is removed for the testing or measuring by means of the test apparatus 24, or the atomiser 1 is gripped or received in the holding device 25 without the lower housing part 18. In this way, scattering of the radiation emitted by the emitter 28 is reduced. However, solutions are also possible in which the atomiser 1 is or can be measured together with the lower housing part 18. In particular, solutions are possible in which the atomiser 1 is or can be tested when (fully) assembled. For example, the lower housing part or cover 18 can be transparent or allow the emitted and reflected radiation to pass through. The sensor 29 is preferably designed to detect at least some of the radiation emitted by the emitter 28 and/or reflected on the container 3 or container bottom 21.

As a result of the radiation being reflected on the container 3 or container bottom 21 and the reflected radiation being detected by means of the sensor 29, it is possible to determine the distance, or the variable distance during the atomisation process, between the measuring device 27 or a side of the measuring device 27 facing the atomiser 1 and the container 3 or container bottom 21 and/or the stroke $\Delta s_{stroke}$ of the container 3 or the distance change in the event of a stroke movement.

In addition or alternatively to the triangulation, other optical measurement methods or principles can also be used, such as interferometry, the silhouette procedure and/or camera-based segmentation. In particular, the movement of the container 3 or container bottom 21, particularly preferably the velocity $v_{stroke}$, the stroke $\Delta s_{stroke}$ and/or the duration $\Delta t_{stroke}$ of the stroke, can be measured, in addition or alternatively to the triangulation, by means of other optical measurement methods, such as interferometry, the silhouette procedure and/or camera-based segmentation.

For example, the test apparatus 24 or measuring device 27 can comprise an (additional) emitter and an (additional) sensor, the container 3 preferably being arranged between the emitter and the sensor and/or being illuminated by the emitter such that a shadow or silhouette of the container 3 or a movement of the container 3 when the fluid 2 is dispensed is detected by the sensor by means of the change in the shadow or silhouette.

According to another embodiment (not shown), the container 3 preferably comprises at least one marking on the side, in particular a line marking, the movement of the container 3 when the fluid 2 is dispensed preferably being measured or tracked by means of the marking and an associated (additional) recording device, in particular a camera.

Preferably, in an embodiment of this kind, the data processing device 31 is designed to detect the position of the marking before the fluid 2 is dispensed, while it is being dispensed and/or thereafter, and/or to segment the image of the container 3 or marking, in particular to perform an edge detection thereon.

In addition or alternatively to optical measurement methods or principles, mechanical and/or electrical measurement methods or principles can also be used. In particular, the movement of the container 3 or container bottom 21, in particular the velocity $v_{stroke}$, the stroke $\Delta s_{stroke}$ and/or the duration $\Delta t_{stroke}$ of the stroke, can be measured, in addition or alternatively to optical measurement methods, by means of mechanical and/or electrical measurement methods.

For example, the movement and/or position of the container 3 can be detected by means of at least one tactile sensor or sensor probe before the fluid 2 is dispensed, while it is being dispensed and/or thereafter.

In another embodiment (not shown), the movement of the container 3 or a distance change of the container 3 can be measured inductively or by means of an inductive sensor.

Preferably, the container 3 in an embodiment of this kind comprises an electrically conductive material such as metal, for example on the container bottom 21, and/or the container 3 in an embodiment of this kind consists at least in part of an electrically conductive material such as metal, a varying inductance during a movement of the container 3 or a distance change of the container 3 relative to an associated sensor preferably being detected or being able to be detected.

In another embodiment (not shown), the movement of the container 3 or a distance change of the container 3 can be measured capacitively or by means of a capacitive sensor, a varying capacitance during a movement of the container 3 or a distance change of the container 3 relative to an associated sensor preferably being detected or being able to be detected.

Preferably, a plurality of in particular different measurement methods or principles can be combined. Advantageously, any measurement errors can thus be detected and the measurement accuracy increased.

Preferably, stroke paths or strokes $\Delta s_{stroke}$ of approximately 0.5 mm to 100 mm, particularly preferably of 1 mm to 20 mm, in particular of 4 mm to 12 mm, are measured.

Preferably, when the atomiser 1 is in the tensioned state, the distance between the measuring device 27, in particular a side of the measuring device 27 facing the atomiser 1, or emitter 28 and the atomiser 1 or container 3 or container bottom 21 is more than 5 mm or 10 mm, particularly preferably more than 20 mm or 30 mm, in particular more than 40 mm, and/or less than 200 mm or 150 mm, particularly preferably less than 100 mm, in particular less than 80 mm.

The system 23 or test apparatus 24 preferably comprises a control device 30, the control device 30 preferably being designed to control the measuring device 27, in particular the emitter 28 and/or the sensor 29, in an open- and/or closed-loop manner.

Preferably, the system 23 or test apparatus 24 comprises a data processing device 31 such as a computer, the data processing device 31 preferably being designed to process, store and analyse data or data signals such as measured values or measurement signals, in particular of the measuring device 27, and/or to compare them with target values, in particular a target velocity, a target stroke and/or a target duration, and/or with limits, in particular a maximum and/or minimum velocity, a maximum and/or minimum stroke and/or a maximum and/or minimum duration.

Particularly preferably, the data processing device 31 is designed to identify a faulty atomiser 1 or to (automatically) identify or flag an atomiser 1 as being faulty when the measured values detected by the measuring device 27 do not comply with the target values, in particular a target velocity, a target stroke and/or a target duration, and/or are outside a range defined by the limits, such as a maximum and/or minimum velocity, a maximum and/or minimum stroke and/or a maximum and/or a minimum duration.

Particularly preferably, the measuring device 27 is or can be electrically connected to the control device 30 and/or to the data processing device 31.

Preferably, the system 23 or test apparatus 24 comprises an actuation or trigger device 32 such as an actuator, the actuation device 32 preferably being designed to actuate the atomiser 1 or locking element 8 or the trigger button 8a of the atomiser 1 and/or to trigger the dispensing of the fluid 2.

Preferably, the actuation device 32 is formed as an electric drive. However, other solutions are also possible in this case. Optionally, the trigger device 32 comprises a force measurement device (not shown), the force measurement device in particular being designed to measure the force required to move the locking element 8 for the purpose of triggering the atomiser 1 or to press the trigger button 8a for the purpose of triggering. In the process, the trigger force is measured in particular as a function of the duration of the triggering or actuation process.

Preferably, the actuation device 32 is electrically connected to the control device 30 and/or to the data processing device 31 and/or can be controlled, in particular triggered, by means of the control device 30 and/or the data processing device 31.

Optionally, the system 23 or test apparatus 24 comprises scales (not shown), the scales preferably being designed to determine the weight of the dispensed fluid 2. Particularly preferably, the scales are integrated in the mount of the atomiser 1 within the test apparatus 24 (this is not shown). Preferably, the scales are electrically connected to the control device 30 and/or to the data processing device 31.

Preferably, the holding device 25, the measuring device 27, the control device 30, the actuation device 32 and/or the scales comprise a shared housing 33 and/or the holding device 25, the measuring device 27, the control device 30, the actuation device 32 and/or the scales are integrated in a shared housing 33. This enables or aids a particularly compact construction.

Optionally, the system 23 or test apparatus 24 comprises a tensioning device (not shown), the tensioning device preferably being designed to tension the atomiser 1 or housing part 16 relative to the inner part 17 or lower housing part 18. Most preferably, the atomiser 1 can be tensioned and actuated by means of the test apparatus 24. Preferably, the tensioning device comprises a measuring device, the measuring device being designed to measure the force required to tension the atomiser 1 and/or to measure the torque that has to be overcome in order to rotate the housing part 16 relative to the inner part 17 or lower housing part 18 in order to load the energy storage mechanism. Preferably, the test apparatus 24 is designed such that it is possible, on the test apparatus 24, to carry out a plurality a test cycles consisting of tensioning the atomiser 1 and triggering (actuating the locking element 8 or the trigger button 8a of the atomiser 1) and, generally, to take at least one measurement of the proper functioning in an automated manner during the atomisation.

Optionally, the system 23 or test apparatus 24 comprises a suction device (not shown) or the system 23 or test apparatus 24 is connected to a suction device, the suction device or a connection to the suction device being designed to suction and/or carry away, in particular out of the test apparatus 24, the aerosol dispensed by the atomiser 1, preferably while the atomiser 1 is producing the aerosol or thereafter.

Optionally, the system 23 or test apparatus 24 comprises a recording device 34, the recording device 34 preferably being designed to optically record or take images of the atomiser 1, in particular of the aerosol 14, during dispensing, or to record the dispensing of the aerosol 14 optically or in the form of images.

Preferably, the recording device 34 is or can be electrically connected to the control device 30 and/or to the data processing device 31.

Within the meaning of the present invention, a "recording device" is in particular an optical, photographic, film or video device that is preferably designed to take, record, generate, process, store and/or transmit or send an in particular digital, static, photographic and/or optical image, such as a video, a video sequence, an image or photo, a sequence of images, a still or the like of an object, in particular of the fluid 2 dispensed or of the aerosol 14. Preferably, a recording device within the meaning of the present invention is a camera, in particular a film camera or video camera, a webcam, screencam, digicam, camcorder or the like, and/or a photo camera, and/or a recording device comprises such and/or a camera module.

Below, the method according to the invention for testing the proper functioning of the atomiser 1 will be described in more detail.

The proposed test method is preferably carried out by the proposed system 23 or test apparatus 24. In particular, the system 23 or test apparatus 24 is designed to carry out the proposed method.

In the test method, the atomiser 1 is tested to check it is functioning properly and/or for any faults. In particular, it is ascertained whether and/or to what extent the atomiser 1 is functional and/or fulfils predefined requirements or has predefined functions.

Particularly preferably, faulty atomisers 1 or those having impaired functions are identified and/or (subsequently) discarded. Preferably, the method is carried out during or after the production process, in particular the assembly process, for the atomiser 1.

Figure 4:
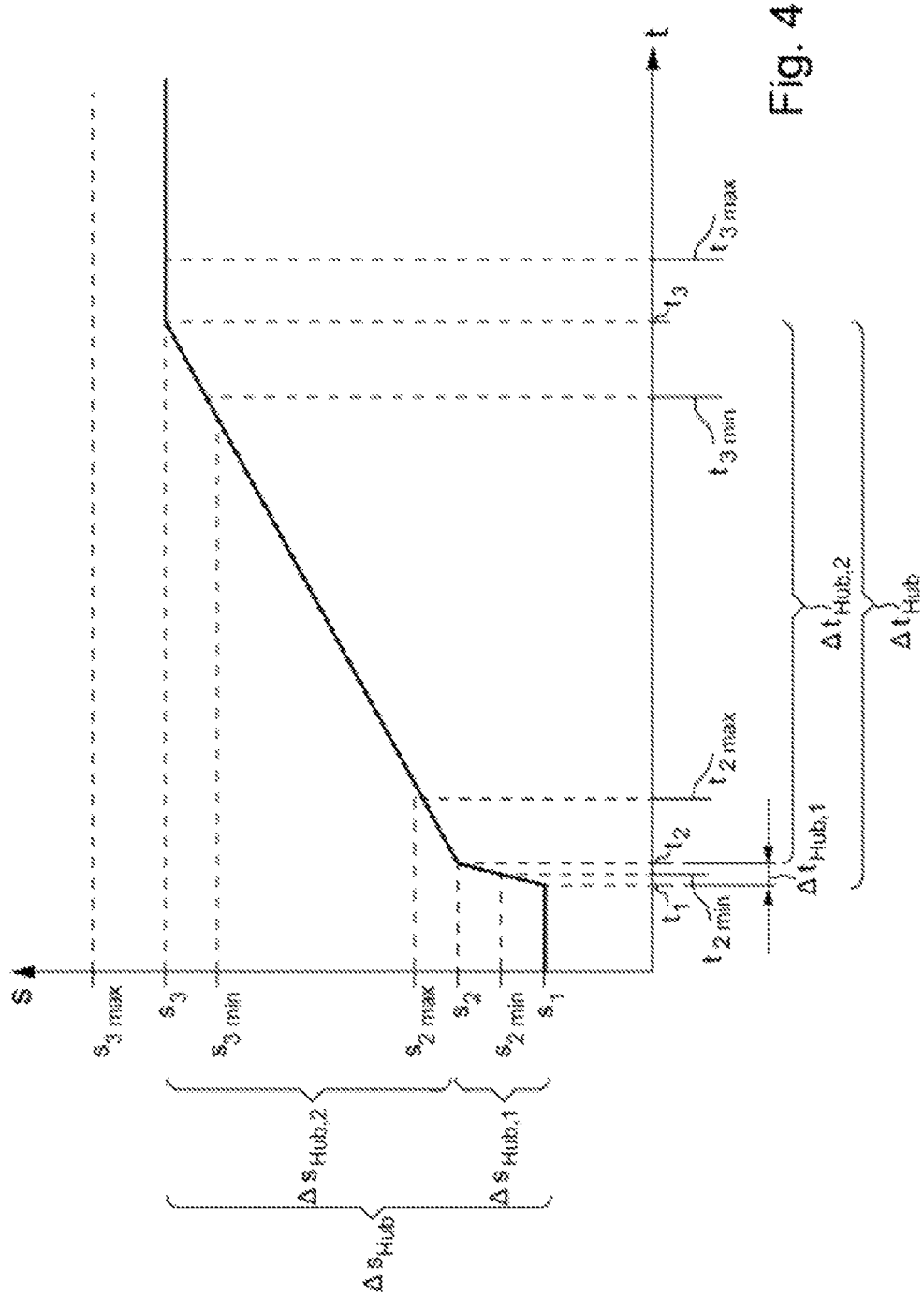
FIG. 4 shows a schematic curve of the container stroke as a function of time.

FIG. 4 shows a schematic or idealised curve of the stroke or path s traveled by the container 3 as a function of time t, the atomiser 1 preferably being actuated or the stroke movement of the container 3 starting at the time $t_1$ and the stroke movement of the container 3 or the dispensing of the fluid 2 ending at time $t_3$.

As shown by FIG. 4, the stroke movement, in particular the stroke $\Delta s_{stroke}$ and the stroke duration $\Delta t_{stroke}$ of the container 3 can in principle be divided into two sectors.

In a first sector $t_1$ to $t_2$ or $s_1$ to $s_2$, the container 3 preferably moves at a higher velocity $v_{stroke}$ than in a second sector $t_2$ to $t_3$ or $s_2$ to $s_3$. In the first sector, the container 3 preferably moves by the idle stroke $\Delta s_{stroke,1}$ for the time $\Delta t_{stroke,1}$. In the first sector, preferably no fluid 2 or only a small amount of fluid is dispensed or atomised. This can be attributed in particular to the compression of possible air bubbles within the atomiser 1, the elastic deformation of the atomiser 1 or of components of the atomiser 1, etc.

In the second sector following the first sector, the container 3 preferably moves by the effective stroke $\Delta s_{stroke,2}$ for the time $\Delta t_{stroke,2}$, the fluid 2 preferably being dispensed or atomised.

Preferably, the idle stroke $\Delta s_{stroke,1}$ and/or the time $\Delta t_{stroke,1}$ is significantly shorter than the time $\Delta t_{stroke,2}$. Particularly preferably, the time $\Delta t_{stroke,1}$ is negligible compared with the time $\Delta t_{stroke,2}$.

The possible faults in the atomiser 1 and/or those that can be measured, identified, quantified, estimated or indexed by means of the test method include in particular a stroke $\Delta s_{stroke}$ or effective stroke $\Delta s_{stroke,2}$ of the container 3 being too short, a velocity of $v_{stroke}$ of the container 3 being too high and/or too low, an idle stroke $\Delta s_{stroke,1}$ of the container 3 being too long, and a duration of spray $\Delta t_{stroke}$ of the atomiser 1 being too short and/or too long. In the process, the following are preferably detected (preferably indirectly) as functional impairments of the atomiser 1: the volume or weight of fluid 2 that leaks out during the dispensing of the fluid 2 being too high, pressure drops in the atomiser 1 being too high, in particular in the supply tube 9 and/or the delivery nozzle 12, the volume or weight of dispensed fluid 2 or aerosol 14 being too low, the flow rate of the fluid 2 in the delivery nozzle 12 being too low, and the velocity at which the aerosol 14 is discharged being too low or too high. Examples of possible causes of leaks that can be detected on the basis of a shorter duration of spray are faulty seals or assembly errors when the components defining the fluid pathway in the atomiser 1 were joined together. By contrast, deposits or incorrect positioning in the fluid pathway (in particular in filters or the nozzle) affecting the functionality would be detected on the basis of a longer duration of spray.

Preferably, the stroke $\Delta s_{stroke}$ of the container 3, in particular the idle stroke $\Delta s_{stroke,1}$ and the effective stroke $\Delta s_{stroke,2}$ of the container 3, the velocity $v_{stroke}$ of the container 3 and the spray or stroke duration $\Delta t_{stroke}$ of the atomiser 1 are directly or immediately measured by means of the test method or detected using corresponding measured values. Preferably, the stroke duration $\Delta t_{stroke}$ and the gradient of a line of best fit in relation to the stroke course in the second sector, i.e. in the time range $t_2$ to $t_3$, measured against time are used as test parameters.

Preferably, the measured values (preferably not only the values or data determined on the measuring device 27, but also those determined on other measuring or recording devices of the test apparatus 24) are then compared with target values and/or target ranges or limits determined preferably empirically, numerically, theoretically and/or practically.

Preferably, the atomiser 1 is (automatically) discarded or identified or classified as being at least substantially faulty or non-functional when the measured values do not comply with the target values and/or are not within the target ranges. In this regard, the system 23 includes an ejection device 50, which operates to cause the atomiser (1) to be automatically slid and/or discarded once detected as being faulty.

If the test apparatus 24 comprises additional measuring devices (not shown) in addition to the measuring device 27 for measuring the movement of the container 3, e.g. scales and/or a measuring device for measuring the force to actuate the trigger button 8a and/or a measuring device for determining the force required to tension the atomiser 1, then the values measured thereby (e.g. weight or force values) are preferably also compared with predetermined and/or specified target values and/or target ranges or limits and atomisers 1 identified as being faulty on the basis of this comparison are preferably discarded. Preferably, optical, photographic or image data detected by the (optional) recording device 34 are also analysed and compared with corresponding data or sets of images defined as limits, and the atomisers 1 identified as being faulty on the basis of such a comparison are discarded.

Preferably, the atomiser 1 is (automatically) identified or classified as being functional or at least substantially fault-free when the measured values comply with the target values and/or are within the target ranges.

To test the atomiser 1, the atomiser 1 is preferably gripped in or received by the test apparatus 24 or holding device 25. Particularly preferably, the atomiser 1 is inserted into the hole 26 in the test apparatus 24 or holding device 25, for example by means of a grip (not shown) or another manipulator (not shown), and is preferably automatically gripped or clamped.

The atomiser 1 preferably comprises an energy storage mechanism such as a spring, the energy storage mechanism preferably being loaded or tensioned in a tensioning process before the atomiser 1 is actuated in order to dispense the aerosol.

Preferably, the atomiser 1 is inserted into or received by the test apparatus 24 or holding device 25 when it is already in the tensioned state. It is also possible, however, for the (non-tensioned) atomiser 1 to be inserted into or received by the test apparatus 24 or holding device 25 first, and to then be tensioned.

In particular, structural solutions are possible in which the test apparatus 24 comprises a tensioning device (not shown), the atomiser 1 or the energy storage mechanism of the atomiser 1 being loaded or tensioned by means of the tensioning device.

Preferably, the atomiser 1 is positioned above or directly in front of the measuring device 27 or emitter 28, in particular such that the container 3 or container bottom 21 can be irradiated.

Preferably, the measuring device 27 is (then) activated or switched on, preferably by means of the control device 30 and/or the data processing device 31. However, it is also possible for the measuring device 27 to be permanently activated or switched on.

Preferably, the container 3 or container bottom 21 is irradiated, in particular by means of the measuring device 27 or emitter 28. Particularly preferably, at least some of the radiation is reflected by or on the container 3 or container bottom 21, preferably at least in part towards the sensor 29.

Particularly preferably, the position of the radiation reflected on the container 3 or container bottom 21 is detected and/or stored in the sensor 29.

Preferably, the distance between the container 3 or container bottom 21 and the measuring device 27 or a side of the measuring device 27 facing the atomiser 1 and/or the change in distance between the container 3 or container bottom 21 and the measuring device 27 or a side of the measuring device 27 facing the atomiser 1 is measured when the fluid 2 is dispensed, preferably by means of the measuring device 27. Preferably, this measurement is carried out before the fluid 2 is dispensed, while the fluid is being dispensed and thereafter, in other words continuously.

Preferably, a measurement signal 35 is generated during the measurement and/or is transmitted to the control device 30 and/or the data processing device 31.

Particularly preferably, measurement signals 35 are generated and/or transmitted continuously, preferably at a frequency of more than 1 kHz or 2 kHz, particularly preferably of more than 5 kHz or 10 kHz, in particular of more than 20 kHz or 50 kHz.

The measurement signal 35 is preferably a signal comprising information on the distance and/or change in distance between the container 3 or container bottom 21 and the measuring device 27, the angle and/or the angular change between the radiation emitted by the emitter 28 and the radiation reflected on the container 3 or container bottom 21, and/or the position and/or change in position of the radiation detected by the sensor 29.

Particularly preferably, the measurement signal 35 comprises information on the stroke $\Delta s_{stroke}$, the velocity $v_{stroke}$ and/or the stroke duration $\Delta t_{stroke}$.

A signal within the meaning of the present invention is preferably a means for transmitting information, a (modulated) wave, in particular in a conductor, a bit sequence, a packet in the IT sense or the like. In particular, a signal within the meaning of the present invention can be transmitted via a transmission medium or by means of a data connection. Preferably, information that can be transmitted by means of a signal is associated with the signal or contained within the signal.

Preferably, the atomiser 1 is actuated in order to dispense the fluid 2, preferably by means of the actuation device 32. By actuating the atomiser 1, the fluid 2 is atomised or the aerosol 14 formed.

Optionally, the force required to tension and/or actuate the atomiser 1 is measured, preferably by means of a measuring device. What is measured in particular is the force required to move the locking element 8 for the purpose of triggering the atomiser 1 or to press the trigger button 8a for the purpose of triggering.

Preferably, the container 3 or container bottom 21 is moved relative to the housing part 16 when the mainspring 7 is relaxed or the fluid 2 is dispensed or the aerosol 14 formed and/or after the atomiser 1 is actuated. In particular, the container 3 or container bottom 21 is moved axially towards the delivery nozzle 12. Particularly preferably, the container 3 or container bottom 21 performs a stroke movement when the fluid 2 is dispensed.

Preferably, the stroke $\Delta s_{stroke}$, the idle stroke $\Delta s_{stroke,1}$, the effective stroke $\Delta_{stroke,2}$, the stroke duration $\Delta t_{stroke}$, the velocity $v_{stroke}$ and/or the acceleration of the container 3 is determined or calculated by means of the measurement signals 35 or measured values, preferably by means of the data processing device 31.

Additionally or alternatively, the pressure drops in the atomiser 1, the flow rate of the fluid 2 in the delivery nozzle 12 and/or the volume or weight of the dispensed fluid 2 is determined or estimated by means of the measurement signals 35 or measured values, preferably by means of the data processing device 31.

Preferably, the measurement signals 35 or measured values, in particular the stroke $\Delta s_{stroke}$, the idle stroke $\Delta s_{stroke,1}$, the effective stroke $\Delta s_{stroke,2}$, the duration $\Delta t_{stroke}$ and/or the velocity $v_{stroke}$ of the container 3 are compared with corresponding target values, in particular a target stroke, a target duration and/or a target velocity, and/or with limits, in particular a maximum and/or minimum stroke, a maximum and/or minimum stroke duration and/or a maximum and/or minimum velocity.

Preferably, the target values and/or limits are stored in the data processing device 31 and/or an (external) database, the data processing device 31 in particular being connected to the database.

Preferably, optical measurements or images are taken of the fluid 2 or aerosol 14 during the dispensing or of the spray pattern produced during the dispensing, preferably by means of the recording device 34 (only shown schematically in FIG. 3), and/or the spray mist or spray/aerosol 14 is optically measured.

Optionally, the spray pattern is transmitted to the data processing device 31 and/or compared with a reference image. In this way, additional faults in the atomiser 1 can be identified, defined and/or assessed, such as faults in the formation of the aerosol cloud or a spray mist that is sharply deflected.

In another aspect of the present invention, which can be implemented independently, the measurement signals 35 or measured values containing the spray pattern recorded by the recording device 34 or the result of the comparison of the spray pattern are combined with the reference image.

In particular, it is checked whether the movement of the container 3 corresponds to the spray pattern or whether a particular movement of the container 3 leads to an expected spray pattern and/or, conversely, whether a particular spray pattern matches an expected movement, movement velocity, etc. of the container 3 or container bottom 21. By combining the available information, it is thus possible in particular to draw a conclusion on the proper functioning of the pressure generator 5 and/or the delivery nozzle 12.

Particularly preferably, the system or test system 23 comprises a spray parameter measuring device for optically measuring the spray mist or spray, the recording device 34 in particular being part of the spray parameter measuring device. Preferably, the spray parameter measuring device is connected to the data processing device 31 and transmitted measurement data are compared therein with reference data.

By means of the spray parameter measuring device, characteristic properties of the droplet cloud or spray or spray mist dispensed by the atomiser 1 are measured. In this case, measured values are preferably generated and compared with defined limits within the system, the atomisers 1 for which the determined measured values are outside the value range defined by the predefined limits in particular being automatically detected as being faulty.

According to a preferred embodiment, the operating principle of the spray parameter measuring device is based on a light section method. In this regard, a light curtain is preferably generated using laser light and cuts through the produced spray mist along a defined plane. Preferably, the light curtain plane extends perpendicularly to the expected main direction of the spray and/or perpendicularly to a longitudinal main axis of the atomiser 1 and/or perpendicularly to the movement direction of the container 3. This sectional plane extends at a defined distance from the nozzle opening of the atomiser 1 or is produced at a defined distance over the mouthpiece 13 of the atomiser 1. When the spray mist or spray passes through the light curtain, the light is scattered on the aerosol droplets of the spray mist, the level of the light scattering being directly dependent in particular on the number of aerosol droplets. As a result, a scattered light image is produced in the light curtain plane. To detect the scattered light image, the system comprises a camera system and/or a recording device 34. Preferably, a plurality of scattered light images are detected over a predefined period of time and at predetermined moments (based on the triggering of the spray mist). Preferably, this period of time corresponds to the expected spray duration, preferably from 1 to 1.5 seconds. A scattered light image is preferably taken at least four times overall; particularly preferably, the scattered light images are taken at regular intervals, e.g. every 0.1 seconds.

Preferably, a conical shape of the expected spray is used as a basis for the analysis of the scattered light images (reference definition). When light is scattered on a conical aerosol cloud of this kind, the intensity of the scattered light increases parabolically towards the centre of the spray cloud. Accordingly, analysis parameters and associated limits matching the expected spray contour are defined. Analysis parameters of this kind are, for example, a cumulative scattered light intensity, the location of the intensity centre in relation to the main axis and the intensity distribution or variance in the scattered light.

By means of a spray parameter measuring device of this kind, the formation of the spray mist can be monitored such as to identify quality defects attributed, for example, to blocked, incorrectly assembled or even damaged nozzles, or to deposits in the region of the nozzle.

Optionally, the weight of the atomiser 1 is detected or measured, preferably before the fluid 2 is dispensed, while the fluid 2 is being dispensed and/or after the fluid 2 has been dispensed, in particular by means of scales. Particularly preferably, however, such weight measurements are part of a subsequent laboratory inspection carried out on selected samples of atomisers 1 that have in particular already been tested in the test apparatus 24.

By calculating the difference between the measured weight of the atomiser 1 and/or of the system 23 or test apparatus 24, in particular the holding device 25, before the fluid 2 is dispensed, and the measured weight of the atomiser 1 and/or of the system 23 or test apparatus 24, in particular the holding device 25, after the fluid 2 has been dispensed, the weight of the dispensed fluid 2 can be determined or estimated.

Optionally, the measured or calculated weight or volume of the dispensed fluid 2 or aerosol 14 is compared with target values or limits, preferably by means of the data processing device 31.

Individual aspects and features of the proposed invention and the described method steps can be implemented either independently of one another or in any combination.

LIST OF REFERENCE NUMERALS 1 atomiser
2 fluid
3 container
4 fluid chamber
5 pressure generator
6 mount
7 mainspring
8 locking element
8a trigger button
9 supply tube
10 return valve
11 pressure chamber
12 delivery nozzle
13 mouthpiece
14 aerosol
15 fresh air opening
16 housing part 17 inner part
17a upper part (inner part)
17b lower part (inner part)
18 lower housing part
19 holding element
20 spring
21 container bottom
22 piercing element
23 system
24 test apparatus
25 holding device
26 hole
27 measuring device
28 emitter
29 sensor
30 control device
31 data processing device
32 actuation device
33 housing
34 recording device
35 measurement signal
s path
$\Delta s_{stroke}$ stroke
$\Delta s_{stroke,1}$ idle stroke
$\Delta s_{stroke,2}$ effective stroke
t duration
$\Delta t_{stroke}$ stroke duration
$v_{stroke}$ stroke velocity

The invention claimed is:

1. A system (23) for testing the proper functioning of a device, wherein the system (23) comprises:
   an atomiser (1) for dispensing a fluid (2) in the form of an aerosol (14), wherein the atomiser (1) is the device and comprises an insertable and replaceable container (3) holding the fluid (2), and a housing part (16), the container (3) being movable relative to the housing part (16) in order to dispense the fluid (2);
   an automated test apparatus (24) including a measuring device (27) for measuring the movement of a container bottom (21) of the container (3) when the fluid (2) is dispensed;
   a data processing device (31) operatively connected to the measuring device (27) and operating to: (i) analyse measured values detected by the measuring device (27), (ii) compare the measured values with target values and/or limits, and (iii) automatically identify whether the atomiser (1) is faulty when the measured values do not comply with the target values and/or the limits; and
   an ejection device by which the atomiser (1) is automatically discarded once detected as being faulty, wherein
   the system automatically moving the atomiser (1) into the test apparatus (24)
   the system automatically causes the atomiser (1) to enter a tensioned state in which the atomiser (1) is ready to dispense the fluid (2) when actuated,
   the system automatically actuates the atomiser (1) to release from the tensioned state and dispense the fluid (2),
   the system automatically measures the movement of the container bottom (21) as the atomiser (1) dispenses the fluid (2), obtains the measured values, compares the measured values with target values and/or limits, and identifies whether the atomiser (1) is faulty, and
   the system automatically ejects the atomiser (1) when the atomiser (1) is faulty.

2. The system (23) according to claim 1, wherein the measuring device (27) is designed to measure at least one of: the velocity ($v_{stroke}$) of the container (3), the stroke ($\Delta s_{stroke}$) of the container (3), and the duration ($\Delta t_{stroke}$) of the stroke ($\Delta s_{stroke}$).

3. The system (23) according to claim 1, wherein:
   the test apparatus (24) comprises, in addition to the measuring device (27), a spray parameter measuring device for taking measurements on at least one of: the aerosol cloud produced by the atomiser (1), and the spray mist produced by the atomiser (1), and
   the test apparatus (24) comprises a recording device (34) for generating images of the aerosol cloud produced by the atomiser (1) or of the spray mist produced by the atomiser (1).

4. The system (23) according to claim 3, wherein:
   the spray parameter measuring device and the recording device are connected to the data processing device (31) of the system (23), and
   the data processing device (31) is designed to analyse measured values detected by the spray parameter measuring device or images generated by the recording device, to compare them with target values, limits or reference images, and to automatically identify the atomiser (1) as being faulty when the measured values or images detected do not comply with the target values, reference images, or the limits.

5. The system (23) according to claim 3, wherein the spray parameter measuring device generates a light curtain that cuts through a defined plane in a spray mist produced by the atomiser (1) or a cloud formed by the aerosol (14).

6. The system (23) according to claim 1, wherein the fluid (2) in the container (3) is a pure ethanol.

7. The system (23) according to claim 1, wherein the test apparatus (24) comprises a holding device (25) for holding or gripping the atomiser (1), a control device (30), and an actuation device (32) for actuating the atomiser (1).

8. The system (23) according to claim 1, wherein the measuring device (27) is designed as an optical measuring device and includes an emitter (28) and a sensor (29).

9. The system (23) according to claim 1, wherein the measuring device (27) contains a laser triangulation sensor system.

10. A method for automatically testing the proper functioning of an atomiser (1) for dispensing a fluid (2) in the form of an aerosol (14), wherein the atomiser (1) comprises an insertable and replaceable container (3) holding the fluid (2), and a housing part (16), and wherein the container (3) is moved relative to the housing part (16) in order to dispense the fluid (2), and the method comprising:
   automatically moving the atomiser (1) into a test apparatus (24), where the test apparatus (24) includes a measuring device (27) for measuring the movement of a container bottom (21) of the container (3) when the fluid (2) is dispensed;
   automatically causing the atomiser (1) to enter a tensioned state in which the atomiser (1) is ready to dispense the fluid (2) when actuated;
   automatically actuating the atomiser (1) to release from the tensioned state and dispensing the fluid (2);
   automatically measuring the movement of the container bottom (21) when the fluid (2) is dispensed;
   automatically obtaining measured values relating to the atomiser (1) dispensing the fluid (2);
   automatically analyzing and comparing the measured values, detected when the container bottom moves, with target values and limits, automatically identifying the atomiser (1) as being faulty when the measured values do not comply with the target values and/or are outside a range defined by the limits, and automatically ejecting the atomiser (1) when identified as being faulty.

11. The method according to claim 10, wherein:

the measuring includes measuring at least one of the velocity ($v_{stroke}$), the stroke ($\Delta s_{stroke}$), and the duration ($\Delta t_{stroke}$) of the stroke ($\Delta s_{stroke}$) by means of a measuring device (27), and the analyzing and comparing are carried out by means of a data processing device (31), with at least one of: a target velocity, a target stroke, a target duration, and/or with a maximum, a minimum velocity, a maximum stroke, a minimum stroke, a maximum duration, and a minimum duration, in order to determine whether the atomiser (1) is functioning properly.

12. The method according to claim 10, further comprising:

gripping or clamping the atomiser (1) by means of a holding device (25), and actuating the atomiser (1) by means of an actuation device (32), in order to dispense the fluid (2).

13. The method according to claim 10, further comprising at least one of:

measuring the weight of the dispensed fluid (2) or of the aerosol (14) by means of scales, taking optical measurements of the fluid (2) or aerosol (14) during the dispensing by means of a spray parameter measuring device, taking images of the fluid (2) or aerosol (14) during the dispensing by means of a recording device (34), and comparing a detected weight value or detected characteristic spray data with at least one of: a target value, the image, and a spray pattern with a reference image.

14. The method according to claim 10, further comprising contactlessly measuring the movement of the container bottom (21), by way of at least one of: the velocity ($v_{stroke}$), the stroke ($\Delta s_{stroke}$), and the duration ($\Delta t_{stroke}$) of the movement or stroke ($\Delta s_{stroke}$), wherein the contactlessly measuring is carried out optically and/or by triangulation by means of a measuring device (27).

15. The method according to claim 10, further comprising irradiating the container bottom (21) by means of a measuring device (27) during the measurement by way of electromagnetic waves being reflected on or by the container bottom (21), by a reflective coating of the container (3).

16. An apparatus for testing the proper functioning of an atomiser (1) for dispensing a fluid (2) in the form of an aerosol (14), wherein the atomiser (1) comprises an insertable and replaceable container (3) holding the fluid (2), and a housing part (16), and wherein the container (3) is moved relative to the housing part (16) in order to dispense the fluid (2), the test apparatus, comprising:

a test apparatus (24) including: (i) a measuring device (27) for measuring the movement of a container bottom (21) of the container (3) when the fluid (2) is dispensed, (ii) a spray parameter measuring device for taking measurements on at least one of the aerosol cloud produced by the atomiser (1), and the spray mist produced by the atomiser (1), using a light curtain, and (iii) a recording device (34) for generating images of the aerosol (14) resulting from the light curtain of the spray parameter measuring device; and a data processing device (31) operatively connected to the measuring device (27) and operating to: (i) analyse measured values detected by the measuring device (27), (ii) compare the measured values with target values and/or limits, and (iii) identify whether the atomiser (1) is faulty when the measured values do not comply with the target values and/or the limits, wherein the data processing device (31) operates to analyse the images of the aerosol (14) resulting from the light curtain, compare the images of the aerosol (14) against target values, limits and/or reference images to identify whether the atomiser (1) is faulty.

17. The apparatus according to claim 16, wherein the test apparatus (24) is suitable for use in a 100% inspection.

18. An apparatus for testing the proper functioning of an atomiser (1) for dispensing a fluid (2) in the form of an aerosol (14), wherein the atomiser (1) comprises an insertable and replaceable container (3) holding the fluid (2), and a housing part (16), and wherein the container (3) is moved relative to the housing part (16) in order to dispense the fluid (2), the test apparatus, comprising:

a test apparatus (24) including a measuring device (27) for measuring the movement of a container bottom (21) of the container (3) when the fluid (2) is dispensed; and a data processing device (31) operatively connected to the measuring device (27) and operating to: (i) analyse measured values detected by the measuring device (27), (ii) compare the measured values with target values and/or limits, and (iii) identify whether the atomiser (1) is faulty when the measured values do not comply with the target values and/or the limits, wherein the measuring and analyzing is carried out for two separate sectors of time, a first sector being when relatively little dispensing occurs at a start of a stroke, and a second sector being when dispensing occurs after first sector is complete, and wherein the container (3) moves at a higher velocity in the first sector than in the second sector.

* * * * *